United States Patent
Bjarnason

(10) Patent No.: US 7,118,602 B2
(45) Date of Patent: Oct. 10, 2006

(54) SUSPENSION LINER HAVING EXTERNAL SURFACE PERIPHERAL PROFILES

(75) Inventor: Asmundur Bergmann Bjarnason, Reykjavik (IS)

(73) Assignee: Ossur hf, Reykjavik (IS)

( * ) Notice: Subject to any disclaimer, the term of this patent is extended or adjusted under 35 U.S.C. 154(b) by 0 days.

(21) Appl. No.: 11/135,330

(22) Filed: May 24, 2005

(65) Prior Publication Data

US 2005/0267599 A1   Dec. 1, 2005

Related U.S. Application Data

(60) Provisional application No. 60/574,948, filed on May 28, 2004.

(51) Int. Cl.
A61F 2/78 (2006.01)
A61F 5/01 (2006.01)
A61F 2/80 (2006.01)

(52) U.S. Cl. ............... 623/32; 623/36; 602/26; 602/63

(58) Field of Classification Search ............ 623/32, 623/33, 34, 35, 36, 37; 602/26, 62, 63; D24/155
See application file for complete search history.

(56) References Cited

U.S. PATENT DOCUMENTS

| | | | |
|---|---|---|---|
| D908,457 | | 1/1909 | Fallon, Jr. |
| 980,457 | A * | 1/1911 | Toles ............... 623/37 |
| D112,752 | S | 12/1938 | Douglas et al. |
| 2,634,424 | A * | 4/1953 | O'Gorman ............... 623/37 |
| 4,161,042 | A * | 7/1979 | Cottingham et al. ...... 623/33 |
| 4,923,474 | A | 5/1990 | Klasson et al. |
| 5,007,937 | A * | 4/1991 | Fishman et al. .......... 623/34 |
| 5,156,464 | A | 10/1992 | Sakai |
| 5,156,629 | A | 10/1992 | Shane et al. |
| 5,246,464 | A | 9/1993 | Sabolich |
| 5,695,452 | A * | 12/1997 | Grim et al. ............... 602/6 |
| 5,742,945 | A * | 4/1998 | Lindaman ............... 2/239 |
| 5,836,308 | A * | 11/1998 | Alla et al. ............. 128/844 |
| D410,742 | S | 6/1999 | Coolidge |
| 5,931,872 | A | 8/1999 | Lohmann |
| 5,980,576 | A | 11/1999 | Graf et al. |
| 6,077,300 | A | 6/2000 | Sabolich et al. |
| D427,684 | S | 7/2000 | Hansson |
| 6,136,039 | A | 10/2000 | Kristinsson et al. |
| 6,485,776 | B1 | 11/2002 | Janusson et al. |
| 6,592,539 | B1 | 7/2003 | Einarsson et al. |
| 6,610,382 | B1 * | 8/2003 | Kobe et al. .............. 428/119 |
| 6,682,569 | B1 | 1/2004 | Wilkinson et al. |
| 6,706,364 | B1 * | 3/2004 | Janusson et al. ......... 428/145 |
| D503,802 | S | 4/2005 | Bjarnason |
| 2002/0120279 | A1 | 8/2002 | Deguillebon et al. |
| 2003/0120279 | A1 | 6/2003 | Hansson |
| 2004/0006346 | A1 | 1/2004 | Holmen et al. |
| 2004/0122528 | A1 | 6/2004 | Egilsson |

(Continued)

OTHER PUBLICATIONS

Iceflex Endurance suction suspension sleeve, Instructions for use, Össur hf.

(Continued)

Primary Examiner—Corrine McDermott
Assistant Examiner—Thomas J. Sweet
(74) Attorney, Agent, or Firm—Bacon & Thomas, PLLC

(57) ABSTRACT

A close-ended residual limb suspension liner includes a distal portion, a proximal portion, and a center portion extending between the distal and proximal portions. An outer surface of the liner includes at least one peripheral profile portion having an undulating wall thickness comprising a plurality of projections arranged in a pattern.

20 Claims, 11 Drawing Sheets

U.S. PATENT DOCUMENTS

2005/0101693 A1* 5/2005 Arbogast et al. ............ 523/122
2005/0125078 A1* 6/2005 Janusson et al. .............. 623/36
2005/0149202 A1* 7/2005 Schaffer et al. ............... 623/36

OTHER PUBLICATIONS

Iceflex Balance suction suspension sleeve, Instructions for use, Össur hf.
Iceross Seal-In Liners, pp. 1-3, downloaded May 5, 2004 at http://www.ossur.com/print.asp?.
Iceflex® Endurance, pp. 1-2, downloaded Apr. 28, 2004 at http://www.ossur.com/template1.asp?pageid=153.
Iceflex® Balance, pp. 1-2, downloaded Apr. 28, 2004 at http://www.ossur.com/template1.asp?pageid=152.
Comfort and Performance start with Iceross(r), pp. 1-2, downloaded May 5, 2004 at http://www.ossur.com/print.asp?.

* cited by examiner

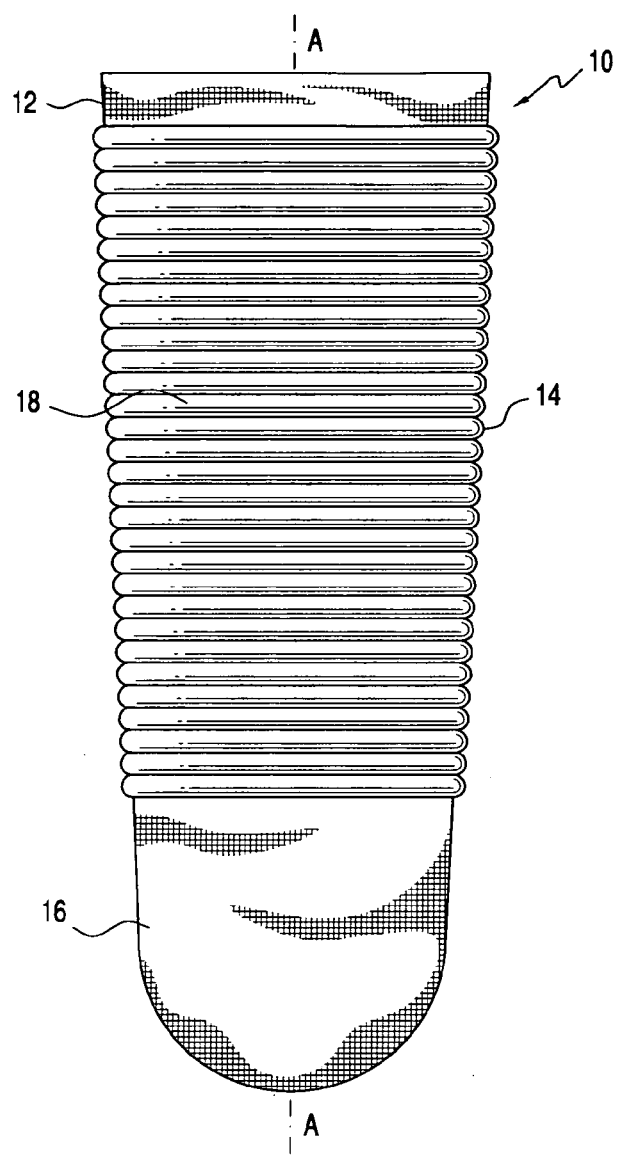
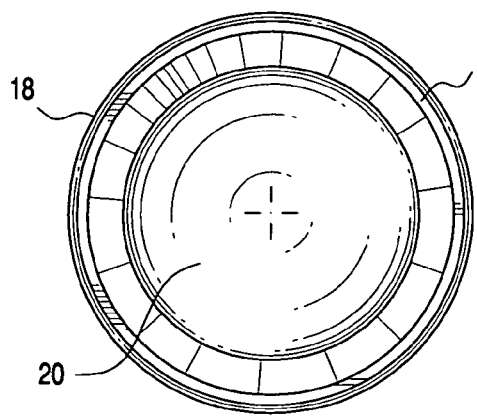 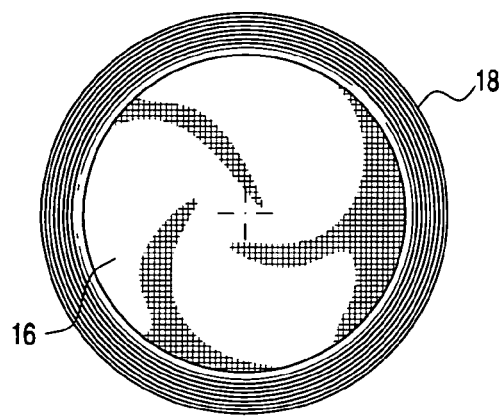
FIG.1
FIG.2　　FIG.3

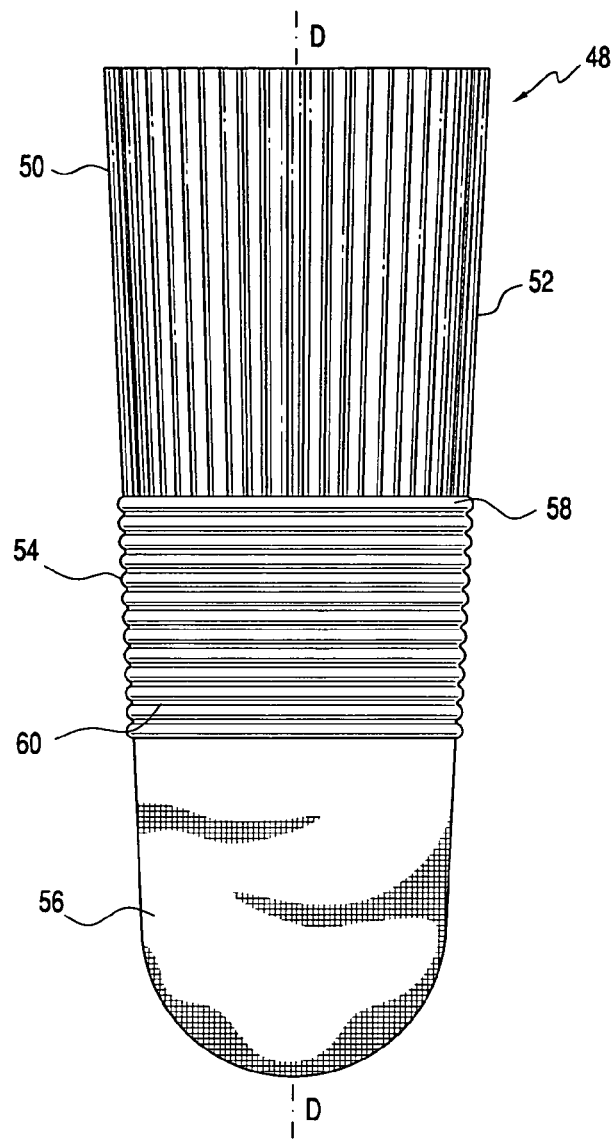
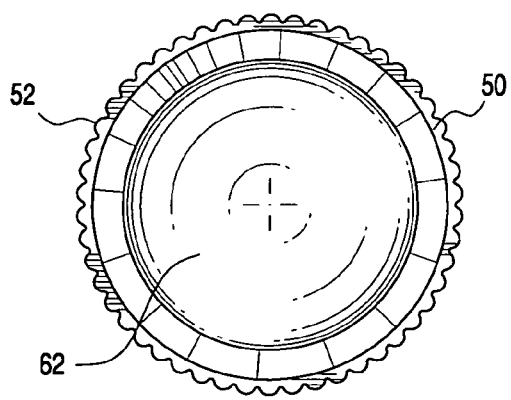 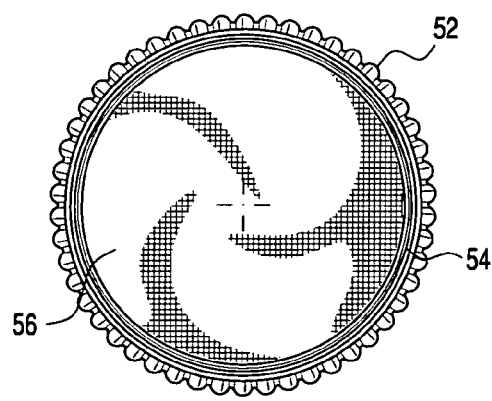
FIG.10
FIG.11　　　　FIG.12

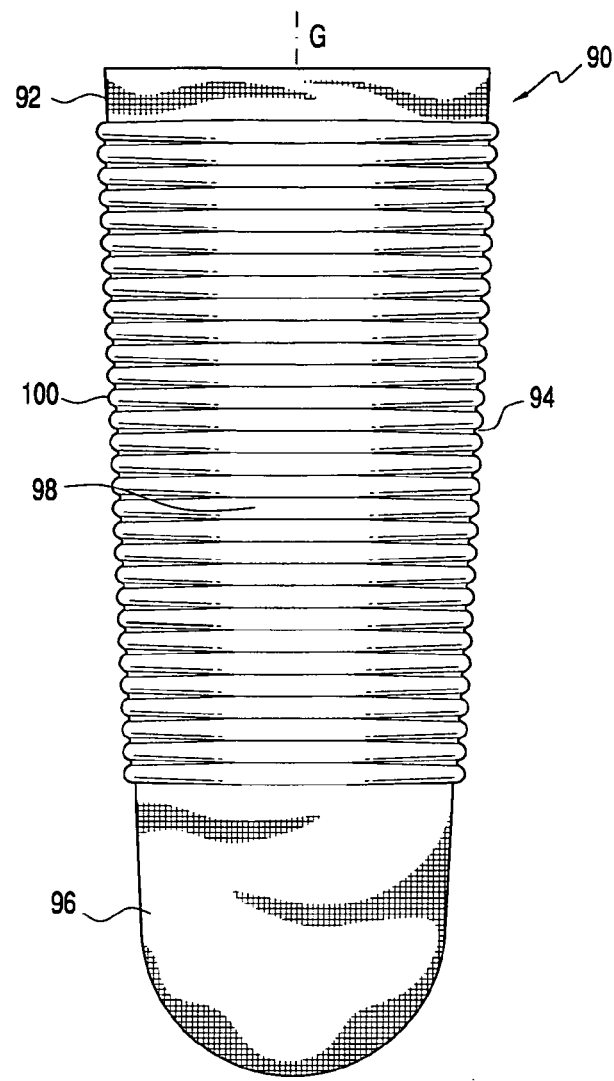
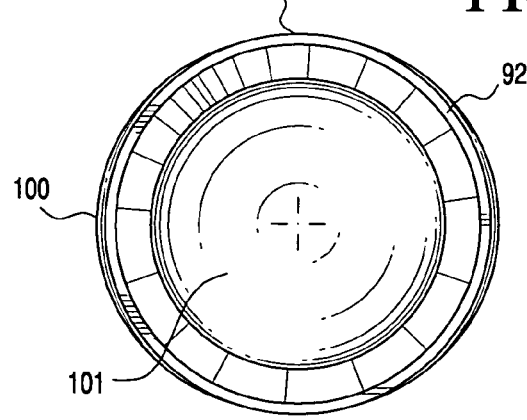
FIG.20
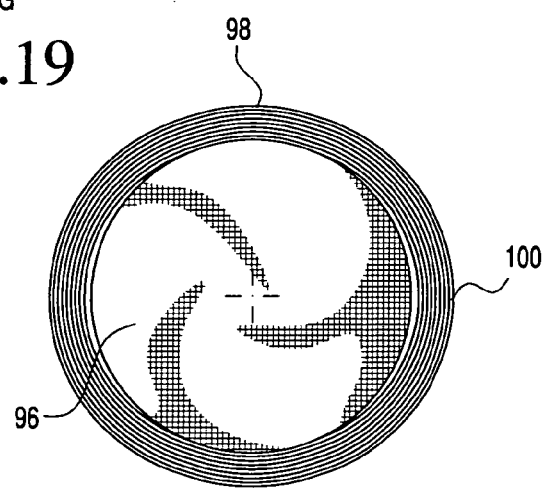
FIG.21
FIG.19

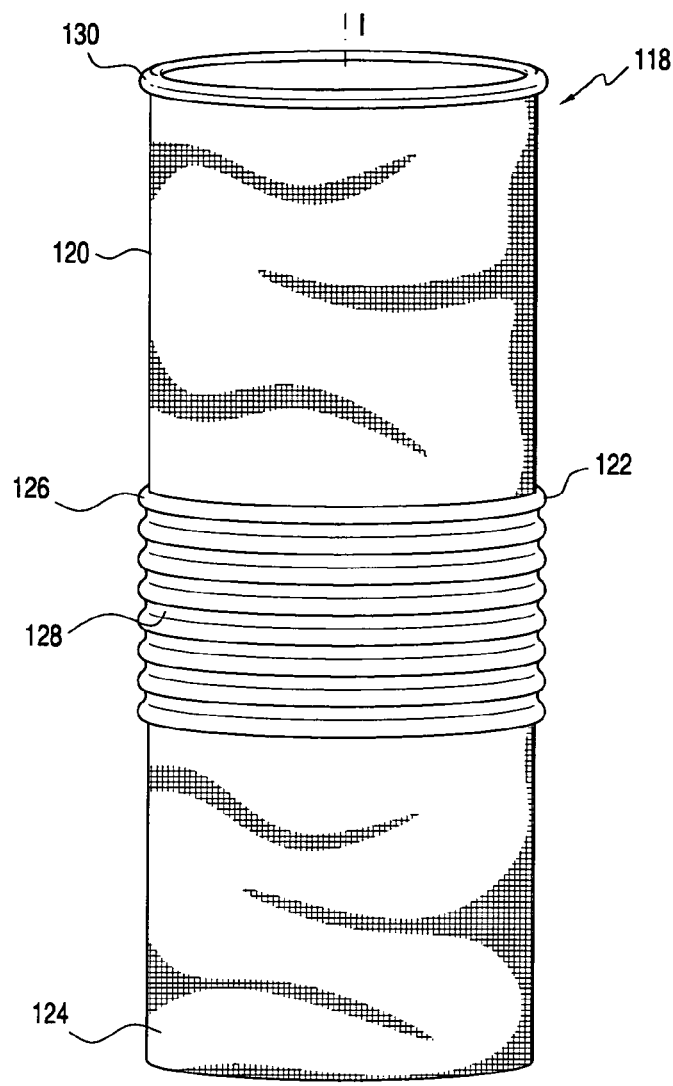
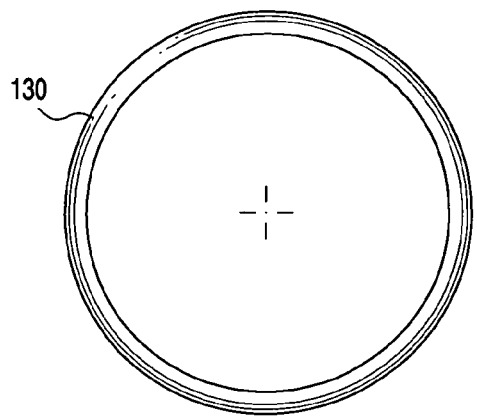 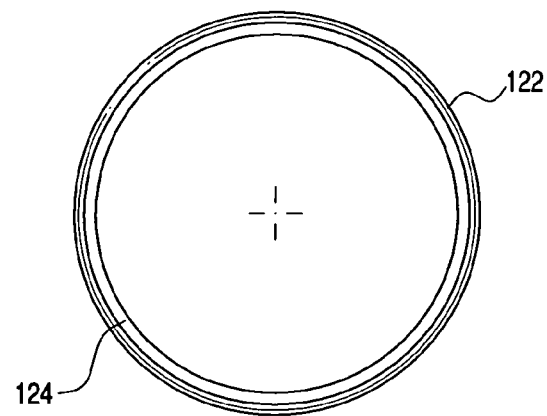
FIG.25
FIG.26  FIG.27

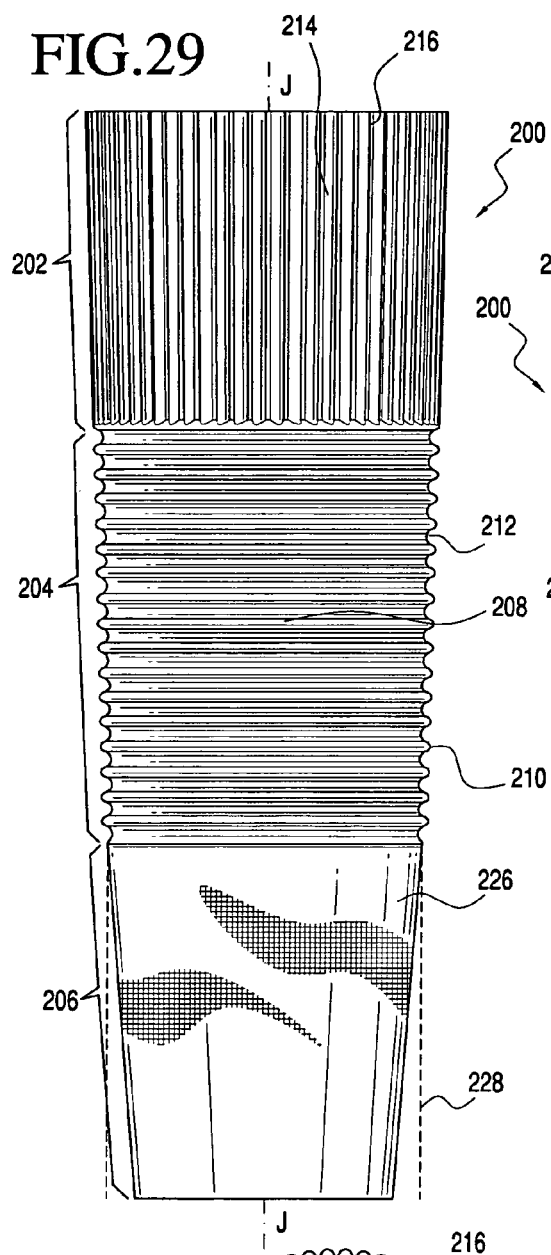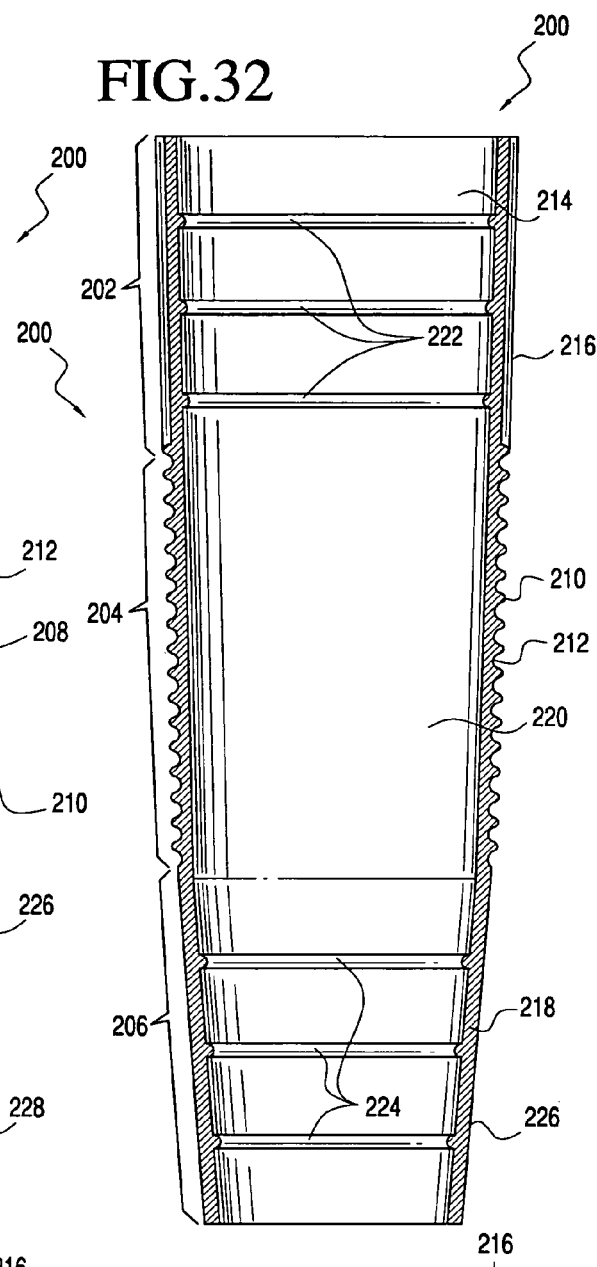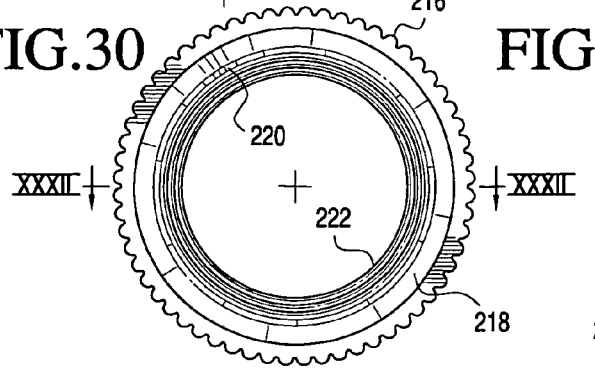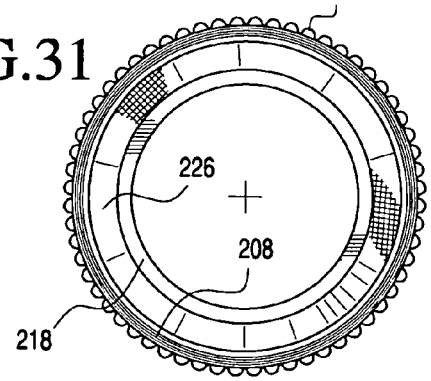

SUSPENSION LINER HAVING EXTERNAL SURFACE PERIPHERAL PROFILES

This application claims the benefit of U.S. provisional application No. 60/574,948 filed May 28, 2004 and is co-pending with U.S. application Ser. No. 11/135,318. This application also relates to U.S. Pat. No. D503,802 granted Apr. 5, 2005.

BACKGROUND

Prosthetic suspension liners have been described in prior patents, such as U.S. Pat. No. 4,923,474 issued May 8, 1990; U.S. Pat. No. 6,136,039 issued Oct. 24, 2000; and U.S. Pat. No. 6,485,776 issued Nov. 26, 2002. These liners may be fabricated of elastic or elasticized materials, and are used to cushion a post-operative stump or residual limb with respect to a prosthesis that is installed over the residual limb and coupled to the sleeve by a conventional locking element.

It is highly desirable that these liners conform closely with the residual limb, accommodate all surface contours and sub-surface bone elements of the residual limb, and provide a comfortable cushion between the residual limb and the hard socket of the prosthesis that is to be fitted over the residual limb.

Special silicone rubber or elastomer materials have been formulated as suitable substances for suspension liners. Such elastomer materials having an appropriate hardness (or softness), elongation, tensile, and other properties, such as bio-inertness (resulting in no skin reaction), have been successfully used for suspension liners.

Much like liners, orthotic or prosthetic sleeves are provided for supporting and reinforcing muscles, joints, and extremities of those in need of assistance, and moreover provide an airtight seal between a residual limb of an amputee and a prosthesis socket worn by the amputee. Moreover, such sleeves are not limited to use for amputees but may be applied to existing limbs to provide support in a manner associated with conventional orthotic devices. Orthotic and prosthetic sleeves of this type are described in U.S. Pat. No. 6,592,539 issued Jul. 15, 2003.

These sleeves may be similarly fabricated of elastic or elasticized materials as in liners. Typically, these sleeves are formed by joining sections of elasticized fabric shaped in tubular form and joined at their axial ends to form a tubular sleeve extending in an axial direction. The sleeves may be cylindrical, curved or possess other anatomically conforming shapes.

While effective solutions have been proposed and implemented, it is still highly desirable to improve comfort of such liners or sleeves to ever so increase their ability to conform to irregularities on a residual limb, to accommodate a wider variety of limbs with fewer sizes of liners, and provide an amputee with enhanced comfort at a residual limb interface with a prosthesis while maintaining sufficient strength and durability. Moreover, it is particularly desirable to provide a liner or sleeve wherein means is made available which distributes pressure of the liner against a prosthesis while providing superior stretchability over known liners and sleeves.

For the foregoing reasons, there is a need to provide improved liners and sleeves that impart improved comformability, pressure distribution, and stretchability while maintaining sufficient durability and strength for their requisite applications.

SUMMARY

The present application is directed to a residual limb suspension liner that satisfies the aforementioned needs. More particularly, an embodiment of a residual limb suspension liner for a prosthesis system is provided which has a closed-ended, air-tight tubular sleeve that is configured to envelop the distal end area of a residual limb. The liner has an axis, and defines a distal portion, a proximal portion, and a center portion extending between the distal and proximal portions. An external surface of the liner is distinguished in that it has at least one peripheral profile portion that is provided for improving the flexion, pressure distribution, comfort and ease of application. The at least one peripheral profile portion results in the liner having an undulating wall thickness at regions corresponding to the peripheral profile portion.

According to variations of this embodiment, individual peripheral profiles of the same portion may assume a variety of configurations and combinations. Configurations may include a plurality of annular protrusions and grooves which extend around the axis of the liner, longitudinal protrusions and grooves which extend between or across the proximal and distal portions of the liner, and protrusions which extend obliquely relative to the axis of the liner.

In another embodiment of a suspension liner, the aforementioned liner includes a recessed portion that extends around at least one peripheral portion of the liner between the proximal and distal portions. A resilient seal element is secured within the recessed portion and protrudes radially therefrom such that the resilient seal element extends around the recessed portion.

The present application is also directed to a prosthetic or orthotic sleeve that also satisfies the aforementioned needs. More specifically, a tubular shaped elasticized fabric defining an open-ended tubular sleeve is provided which extends along an axis, and defines a distal portion, a proximal portion, and a center portion extending between the distal and proximal portions. An external surface of the sleeve has at least one peripheral profile portion, such as those described above in connection with the suspension liner, and has an undulating wall thickness along the peripheral profile portion.

Similar to the liner, the prosthetic or orthotic sleeve includes different embodiments wherein the peripheral profile portion assumes a variety of configurations and combinations.

In a variation of both the suspension liner and prosthetic or orthotic sleeve of the present invention, variations thereof may define at least one sealing ring on along their internal surface. This sealing ring provides enhanced sealing properties when the liner or sleeve is worn against skin, and conforms to variously shaped limbs and prosthetic components. This is particularly evident in view of the soft and compressive nature of silicone which is preferably used as the internal surface of the liner or sleeve. According to one variation, a plurality of sealing rings are formed along the proximal and distal portions of the liner or sleeve. In this variation, the center portion does not include any sealing rings since the center portion is likely to be placed over a knee portion of a prosthesis system, hence be subject to flexure.

The improved liners and sleeves overcome deficiencies in the known liners and sleeves. Due to the peripheral profiles, these liners and sleeves provide improved comformability, pressure distribution, and stretchability while maintaining sufficient durability and strength for their requisite applications. More specifically, a peripheral profile portion at the center portion of the liner or sleeve ensures minimal knee restriction since the peripheral profiles impart greater flexibility to the liner or sleeve. On the other hand, a peripheral profile portion at the proximal portion provides constant pressure and relief about an upper leg portion.

BRIEF DESCRIPTION OF THE DRAWINGS

These and other features, aspects, and advantages of the present invention will become better understood with regard to the following description, appended claims, and accompanying drawings where:

FIG. 1 is an elevational view of a suspension liner embodying features of the present invention;

FIG. 2 is a top plan view of the suspension liner of FIG. 1;

FIG. 3 is a bottom plan view of the suspension liner of FIG. 1;

FIG. 10 is an elevational view of another version of a suspension liner of the invention;

FIG. 11 is a top plan view of the suspension liner of FIG. 10;

FIG. 12 is a bottom plan view of the suspension liner of FIG. 10;

FIG. 19 is an elevational view of another version of a suspension liner of the invention;

FIG. 20 is a top plan view of the suspension liner of FIG. 19;

FIG. 21 is a bottom plan view of the suspension liner of FIG. 19;

FIG. 25 is an elevational view of a prosthetic or orthotic sleeve embodying features of the present invention;

FIG. 26 is a top plan view of the prosthetic or orthotic sleeve of FIG. 25;

FIG. 27 is a bottom plan view of the prosthetic or orthotic sleeve of FIG. 25;

FIG. 29 is an elevational view of another version of a prosthetic or orthotic sleeve of the invention;

FIG. 30 is a top plan view of the prosthetic or orthotic sleeve of FIG. 29;

FIG. 31 is a bottom plan view of the prosthetic or orthotic sleeve of FIG. 29; and FIG. 32 is a section view taken along line XXXII—XXXII of FIG. 30.

DETAILED DESCRIPTION OF VARIOUS EMBODIMENTS

Figure 4:
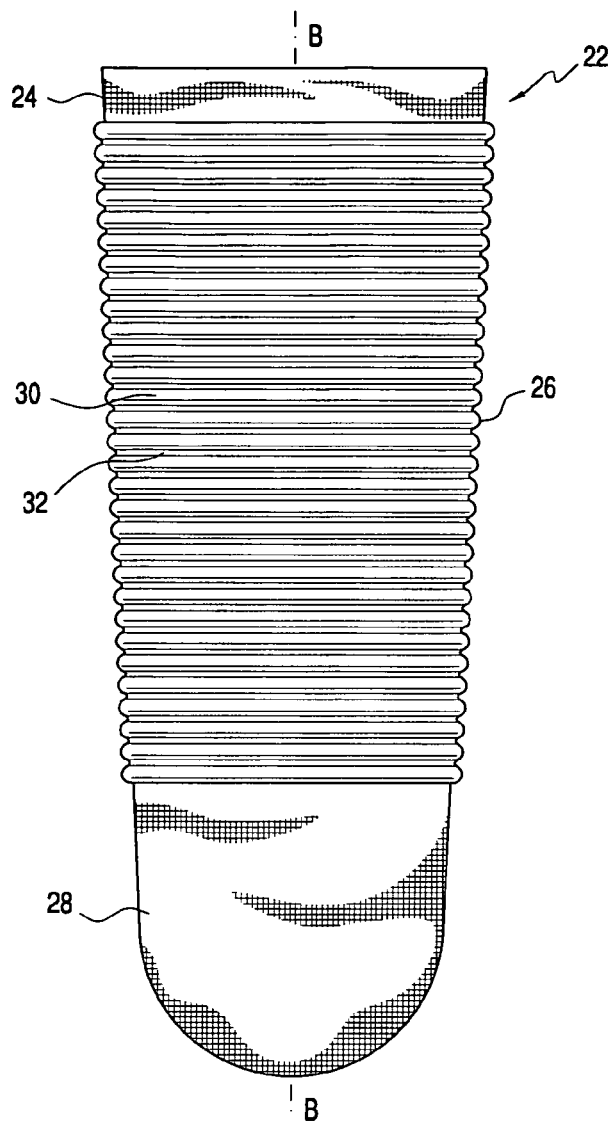
FIG. 4 is an elevational view of another version of a suspension liner of the invention.

A better understanding of different embodiments of the invention may be had from the following description read in conjunction with the accompanying drawings in which like reference characters refer to like elements.

FIGS. 1–3 illustrate an embodiment of a prosthetic suspension liner 10. Referring to FIG. 1, the liner 10 defines a close-ended tubular sleeve having an axis A—A, and is configured to envelop a distal area of a residual limb (not shown). The liner 10 defines a proximal portion 12, a distal portion 16, a center portion 14 axially extending between the proximal and distal portions 12, 16.

An external surface of the liner 10 defines a plurality of peripheral profiles 18 that extend across the center portion 14 and at least a portion of the proximal portion 12. In this embodiment, the distal portion 16 is without the peripheral profiles 18.

The peripheral profiles 18 are defined as a plurality of adjacent projections that extend annularly about the axis of the liner 10. The projections 18 have a generally uniform, rounded outline, and are axially spaced from one another. As shown in FIGS. 2 and 3, the projections 18 generally distend radially beyond adjacent sections of the proximal and distal portions 12, 16, and the internal surface 20 of the liner 10 is substantially smooth.

Figure 5:
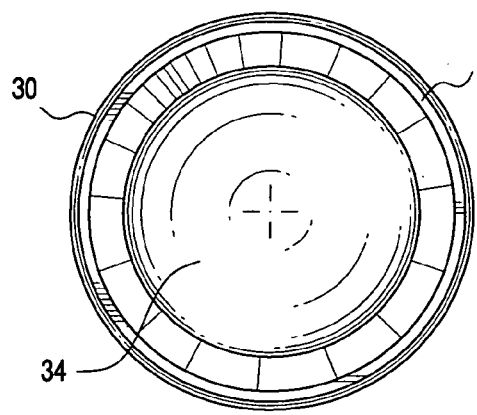
FIG. 5 is a top plan view of the suspension liner of FIG. 4.
Figure 6:
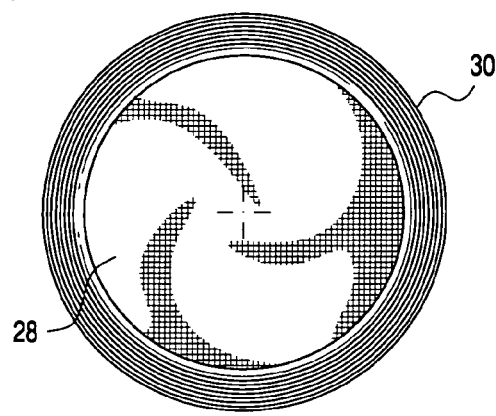
FIG. 6 is a bottom plan view of the suspension liner of FIG. 4.

FIGS. 4–6 illustrate another embodiment of a prosthetic liner 22. Referring to FIG. 4, the liner 22 defines a close-ended tubular sleeve having an axis B—B. The liner 22 includes a proximal portion 24, a distal portion 28, and a center portion 26 axially extending between the proximal and distal portions 24, 28.

An external surface of the liner 22 defines a plurality of peripheral profiles 30, 32 that extend across the center portion 26 and at least a portion of the proximal portion 24. In this embodiment, the distal portion 28 is without the peripheral profiles 30, 32.

The peripheral profiles 30 are defined as a plurality of projections that extend annularly about the axis of the liner 22. The projections 30 have a generally uniform, rounded outline, and are each axially spaced from one another by a groove 32. As shown in FIGS. 5 and 6, the projections 30 and the grooves 32 generally radially distend beyond adjacent sections of the proximal and distal portions 24, 28, and the internal surface 34 of the liner 22 is substantially smooth.

It will be understood, however, that the grooves 32 may be indented into the external surface of the liner 22 relative to the external surfaces of the section of the proximal portion 24 without the projections 30, and the distal portion 28.

Figure 7:
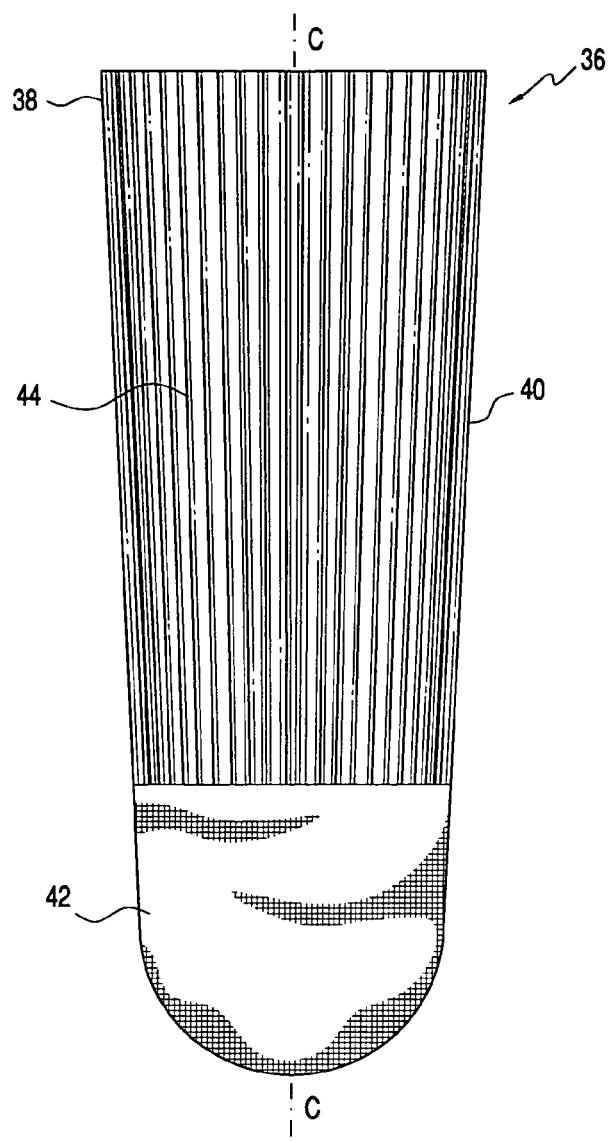
FIG. 7 is an elevational view of another version of a suspension liner of the invention.
Figure 8:
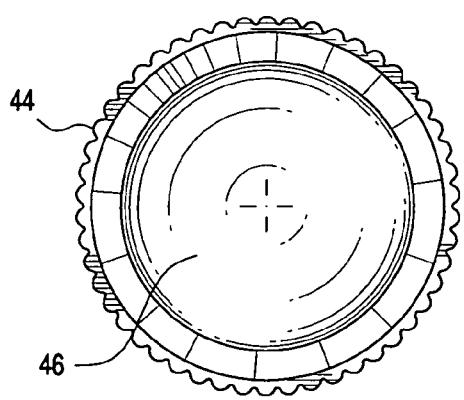
FIG. 8 is a top plan view of the suspension liner of FIG. 7.
Figure 9:
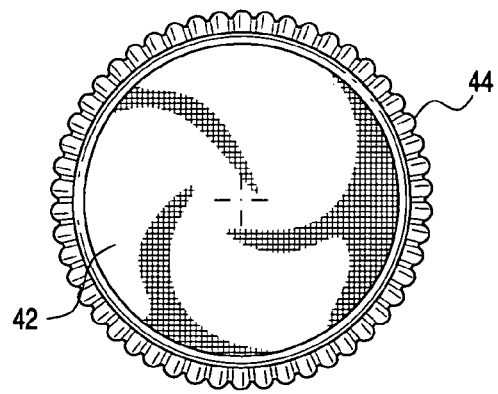
FIG. 9 is a bottom plan view of the suspension liner of FIG. 7.

FIGS. 7–9 illustrate another embodiment of a prosthetic liner 36. Referring to FIG. 7, the liner 36 defines a close-ended tubular sleeve having an axis C—C. The liner 36 includes a proximal portion 38, a distal portion 42, and an axially extending center portion 40 extending between the proximal and distal portions 38, 42.

An external surface of the liner 36 defines a plurality of peripheral profiles 44 that extend across the center portion 40 and the proximal portion 38. In this embodiment, the distal portion 42 is without the peripheral profiles 44. It will be noted in other embodiments having a construction similar to the liner 36, the profiles 44 may extend across only a section of the proximal portion 38 adjacent the center portion 40 such that a section near or at the proximal end of the liner is without peripheral profiles, similar in arrangement to the embodiments shown in FIGS. 1–6.

The peripheral profiles 44 are defined as a plurality of projections that extend longitudinally along the external surface of the liner 36 towards the proximal and distal portions 38, 42, and are circumferentially spaced. The profiles 44 have a generally uniform, rounded outline, and are adjacent to one another.

As shown in FIGS. 8 and 9, the profiles 44 extend outwardly such that they are aligned with the external surface of the distal portion 42 of the liner 36, and the internal surface 46 of the liner 36 is substantially smooth. It will be noted that in alternative embodiments the profiles 44 may distend radially beyond the external surface of the distal portion 42.

FIGS. 10–12 illustrate another embodiment of a prosthetic liner 48. Referring to FIG. 10, the liner 48 defines a close-ended tubular sleeve having an axis D—D. The liner 48 includes a proximal portion 50 and a distal portion 56.

An external surface of the liner 48 defines a first plurality of peripheral profiles 52 that may extend across the proximal portion 50 to generally a mid-length of the liner 48. In this embodiment, the first plurality of peripheral profiles 52 are defined as a plurality of circumferentially spaced projections that extend longitudinally along the external surface of the liner 48. The first plurality of profiles 50 have a generally uniform, rounded outline, and are adjacent to one another.

As shown in FIGS. 11 and 12, the first plurality of profiles 50 extend outwardly such that they are aligned with the external surface of the distal portion 56 of the liner 48. It will be noted, however, that in alternative embodiments the first plurality of profiles 50 may distend radially beyond the external surface of the distal portion 56.

The external surface of the liner 48 also defines a second plurality of peripheral profiles 54 that may extend from a mid-length to the distal portion 56 of the liner 48. The second plurality of peripheral profiles 54 are defined as a second plurality of projections 58 spaced apart by grooves 60 that extend annularly about the axis of the liner 48. Each of the second plurality of projections 58 have a generally uniform, rounded outline.

As shown in FIGS. 11 and 12, the projections 58 and the grooves 60 generally distend radially beyond adjacent sections of the proximal and distal portions 50, 56, and the internal surface 62 of the liner 48 is substantially smooth.

It will be understood that the grooves 60 may be indented into the external surface of the liner 48 relative to the external surfaces of the distal portion 56 of the liner 48.

Figure 13:
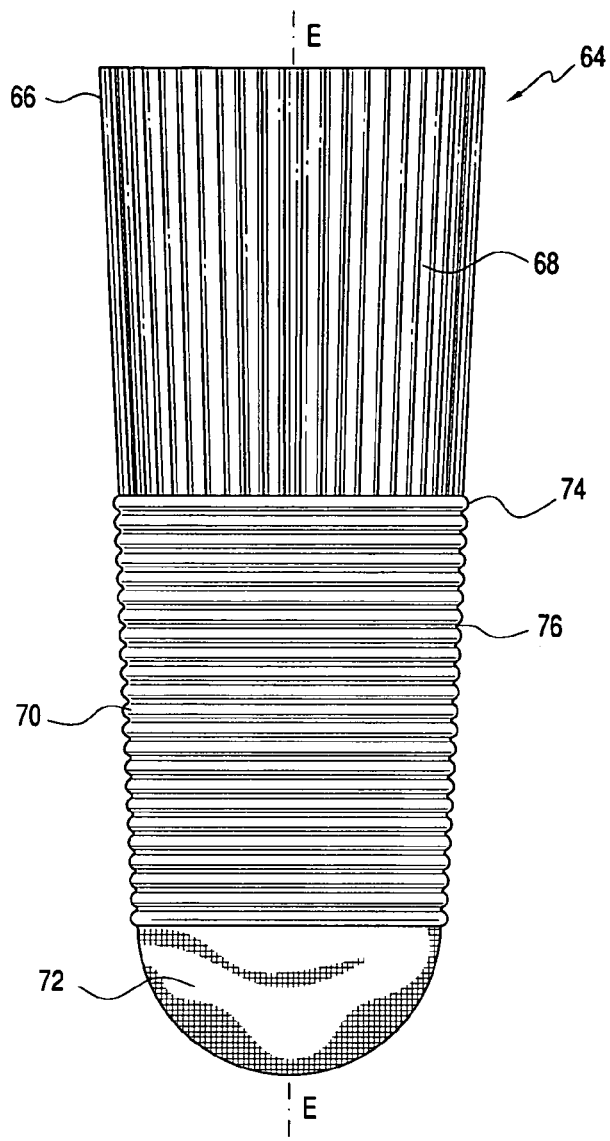
FIG. 13 is an elevational view of another version of a suspension liner of the invention.
Figure 14:
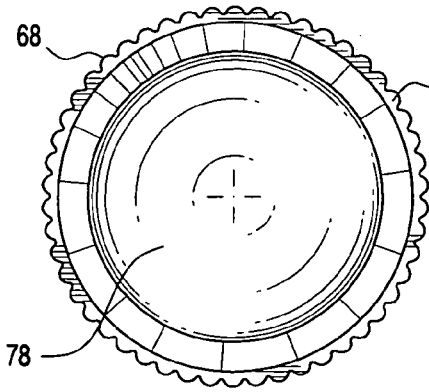
FIG. 14 is a top plan view of the suspension liner of FIG. 13.
Figure 15:
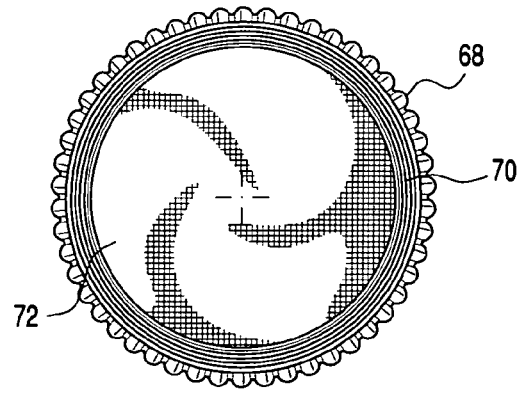
FIG. 15 is a bottom plan view of the suspension liner of FIG. 13.

FIGS. 13–15 illustrate another embodiment of a prosthetic liner 64. This embodiment is similar to the embodiment shown in FIGS. 10–12 such that the external surface of the liner 64 includes a first plurality of longitudinally extending peripheral profiles 68 that extend across a proximal portion 66 of the liner 64 to a generally mid-length of the liner 64, and a second plurality of peripheral profiles 70 defined as a plurality of annularly extending, alternating projections 74 and grooves 76.

The difference of this embodiment from the embodiment shown in FIGS. 10–12 is that the second plurality of peripheral profiles 70 extend across at least a section of a distal portion 72 of the liner 64. As with the other embodiments described thus far, the internal surface 78 of the liner 64 is substantially smooth.

The degree of extension or amount of the second plurality of peripheral profiles 70 extending into the distal portion 72 may be established as one skilled in the art may consider necessary to impart the aforementioned benefits of the inventive liner to a patient having a residual limb.

Figure 16:
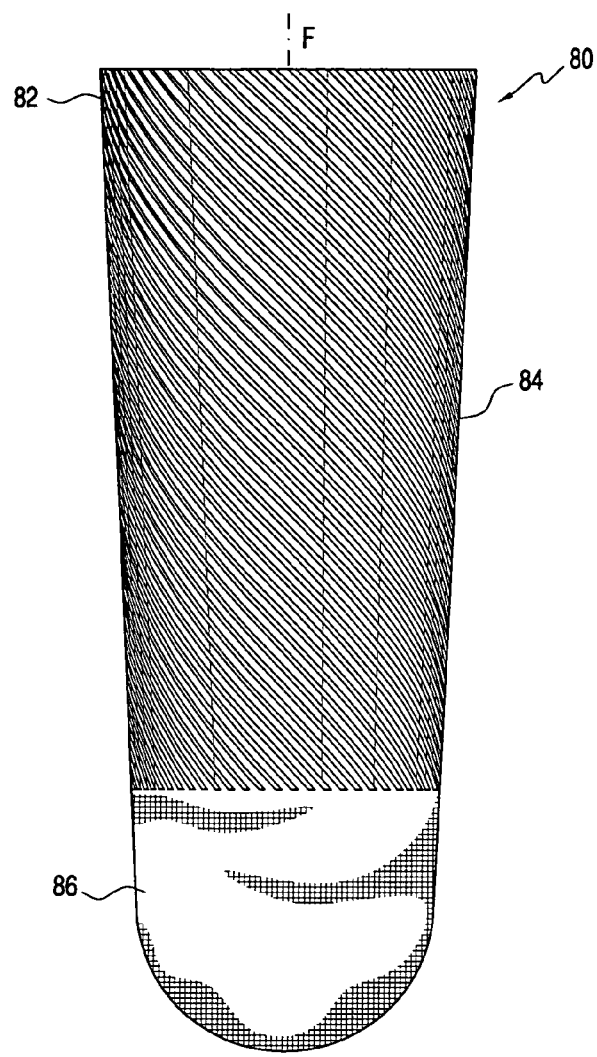
FIG. 16 is an elevational view of another version of a suspension liner of the invention.
Figure 17:
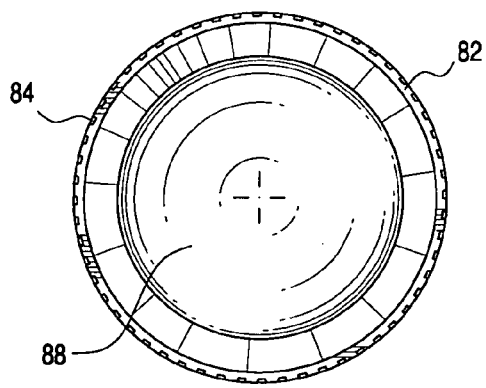
FIG. 17 is a top plan view of the suspension liner of FIG. 16.
Figure 18:
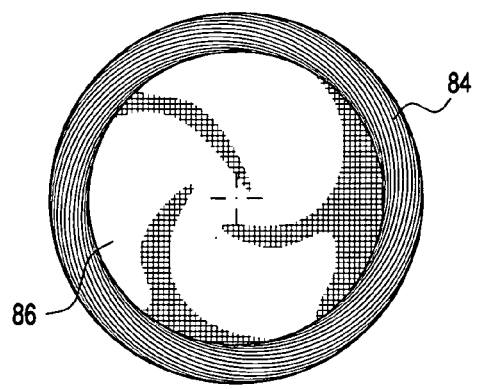
FIG. 18 is a bottom plan view of the suspension liner of FIG. 16.

FIGS. 16–18 illustrate another embodiment of a prosthetic liner 80. Referring to FIG. 16, the liner 80 defines a close-ended tubular sleeve having an axis F—F and configured to envelop a distal end area of a residual limb (not shown). The liner 80 defines a proximal portion 82 and a distal portion 86.

An external surface of the liner 80 defines a plurality of peripheral profiles 84 that extend obliquely relative to the axis of the liner and around the liner. While clearly not intended to be limited to such a configuration, the peripheral profiles 84 extend across the proximal portion 82 of the liner 80 to the distal portion 86 of the liner 80.

The peripheral profiles 84 are defined as a plurality of adjacent projections and have a generally uniform outline. As shown in FIGS. 17 and 18, the peripheral profiles 84 do not distend radially beyond the external surface of the distal portions 86, and the internal surface 88 of the liner 80 is substantially smooth.

While the peripheral profiles 84 are shown as generally extending at a 45° angle relative to the axis F—F, this embodiment is not intended to be limited to such an angle. Accordingly, the angle at which the peripheral profiles 84 extend may be modified accordingly as one skilled in the art may deem necessary to impart the benefits of the inventive liner to a patient wearing such liner.

FIGS. 19–21 illustrate yet another embodiment of a prosthetic liner 90. Referring to FIG. 19, the liner 90 defines a close-ended tubular sleeve having an axis G—G and configured to envelop a distal end area of a residual limb (not shown). The liner 90 defines a proximal portion 92 and a distal portion 96.

An external surface of the liner 90 defines a plurality of peripheral profiles 94 that variably extend about the axis G—G. While clearly not intended to be limited to such a configuration, the peripheral profiles 94 extend across the proximal portion 92 of the liner 90 to about the distal portion 96.

The peripheral profiles 94 are defined as a plurality of adjacent projections 100. This liner 90 has non-profiled portions 98 within the peripheral profiles 94 that lie about the periphery wherein the projections 100 diminish so that the non-profiled portions 98 generally follow the contour of the distal portion 96 of the liner 90. As shown in FIGS. 20 and 21, the peripheral profiles 94 variably distend radially beyond the external surface of the distal portions 96, and the internal surface 101 of the liner 90 is substantially smooth.

It will be understood that in alternative embodiments, the peripheral profiles may have projections that intermittently extend about the axis G—G, and may further radially extend uniformly beyond the external surface of the distal portions of the liner. Moreover, alternate embodiments may have gaps of the projections about the axis wherein certain portions about the periphery have peripheral profiles whereas other portions lack such peripheral profiles. Such gaps may have gradual transitions between the projections or such gaps may be abrupt.

It will also be understood that in concert with the embodiment of liner 90, the projections may be arranged in any of the configurations thus described herein such that there are non-profiled regions within the borders of the peripheral profiles.

Figure 22:
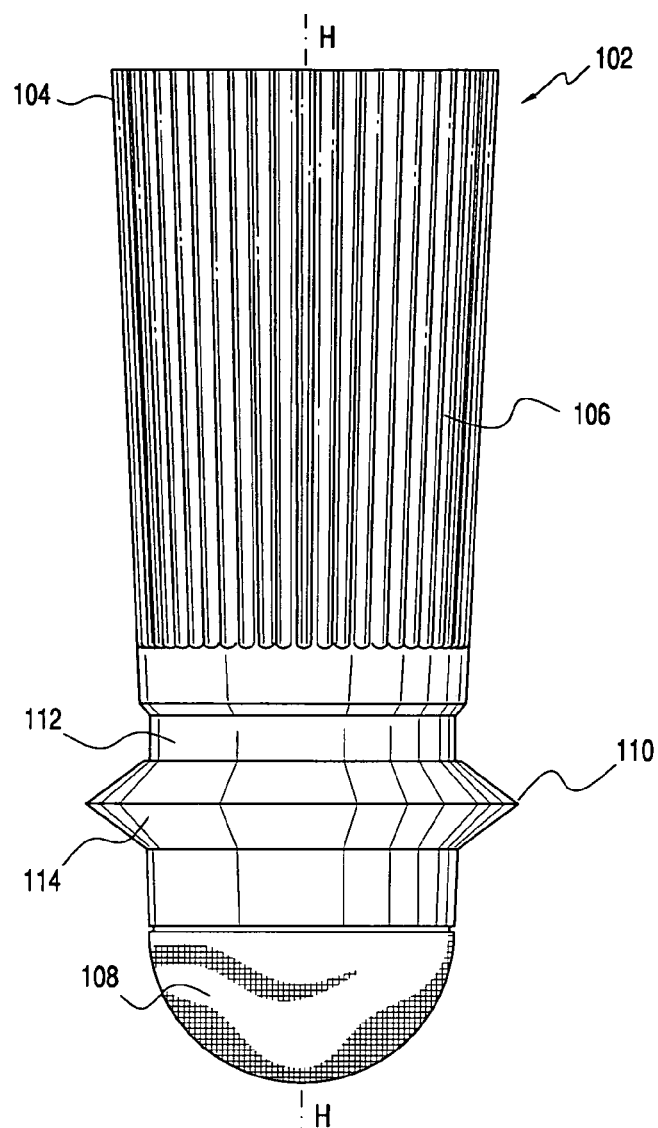
FIG. 22 is an elevational view of another version of a suspension liner of the invention.
Figure 23:
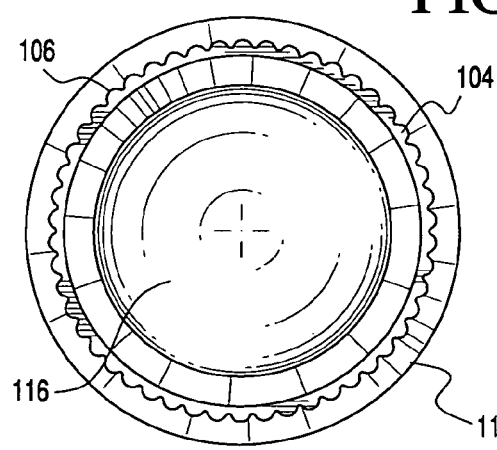
FIG. 23 is a top plan view of the suspension liner of FIG. 22.
Figure 24:
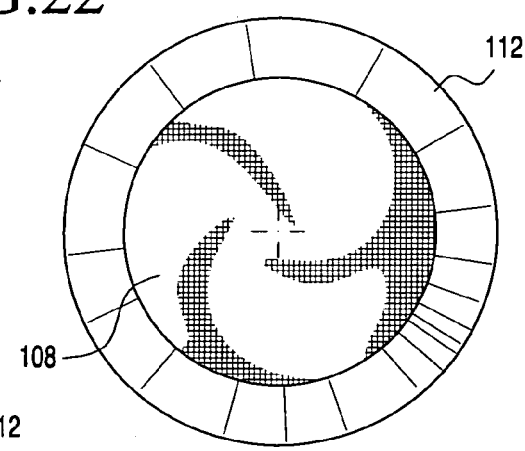
FIG. 24 is a bottom plan view of the suspension liner of FIG. 22.

FIGS. 22–24 illustrate another embodiment of a prosthetic liner 102. This embodiment resembles embodiments of a suspension liner with a seal described in pending U.S. patent application Ser. No. 10/690,545, filed Oct. 23, 2003 which is commonly owned by the assignee of the present application.

The entirety of U.S. patent application Ser. No. 10/690,545 is incorporated herein by reference.

Referring to FIG. 22, the liner 102 defines a close-ended tubular sleeve having an axis H—H. The liner 102 includes a proximal portion 104 and a distal portion 108. An external surface of the liner 102 defines a plurality of peripheral profiles 106 that extend across the proximal portion 104 to a seal portion 110. The peripheral profiles 106 are defined as a plurality of adjacent projections that extend longitudinally along the external surface of the liner 102 towards the proximal and distal portions 104, 108. FIG. 23 illustrates that the profiles 106 have a generally uniform, rounded outline, and are substantially adjacent to one another.

As shown in FIGS. 23 and 24, the profiles 106 extend outwardly such that they are aligned with the external surface of the distal portion 108 of the liner 102, and the internal surface 116 of the liner 102 is substantially smooth. It will be noted that in alternative embodiments the profiles 106 may distend radially beyond the external surface of the distal portion 108.

The seal portion 110 is defined by at least one recessed portion 112 that extends around at least one peripheral portion of the liner 102 between the plurality of peripheral profiles 106 and the distal portion 108. The seal portion 110 also includes at least one resilient seal element 114 that is secured within the at least one recessed portion 112. The at least one resilient seal element 114 protrudes radially from and extends around the at least one recessed portion 112.

The seal liner embodiment shown in FIGS. 22–24 may be modified as discussed in U.S. patent application Ser. No. 10/690,545. The seal liner embodiment provides secure, comfortable suspension without an external sleeve worn over the prosthesis, and thus imparts improved freedom of movement, increased comfort, and simplified maintenance.

While in each of the liner embodiments described above the distal portion is generally without peripheral profiles, liner embodiments of the invention may configured so that at least a section of the distal portion may be provided with peripheral profiles such as those discussed above. It will be noted that, as clearly shown in each of FIGS. 1–24, embodiments of the liner may have variable wall thicknesses at least in regions of the peripheral profiles. Such variable wall thickness improves the ability to stretch the liner and additionally provides cushioning by more aptly distributing pressure against a prosthesis.

Moreover, the peripheral profile portions of the liners may be combined or modified as considered expedient by one of ordinary skill in the art to improve stretchability and comfort for an amputee.

In each of the embodiments shown herein, the liner is intended for use between a residual limb and a prosthesis, and to be air-tight when donned over a residual stump. The internal surface of the liner may be formed of a layer of silicone elastomer, therefore serving as a skin interface. Silicone is advantageous in that is permits different levels and softness and strength to be incorporated into the liners of the present application. Moreover, silicone permits the addition of selected supplements, such as petroleum jelly and aloe vera, which improve skin care and comfort.

An elasticity controlling matrix material may be provided on the exterior of the liner, the matrix material preferably being relatively compliant in a radial direction and substantially rigid or inelastic in an axial direction. The matrix material may extend over the distal or external side of the prosthesis, and is advantageous in that it prevents movement of liner when a prosthesis is worn thereover.

It will be understood that it is envisioned that any of the aforementioned liners, and subsequently discussed sleeves, may be constructed having a soft internal silicone elastomer layer and a relatively harder external silicone elastomer layer in accordance with U.S. Pat. No. 6,136,039, granted Oct. 24, 2000 incorporated herein by reference and owned by the assignee of the present application.

A prosthesis connecting element may be provided at the distal end of any of the embodiments of the inventive liner of the present application. Such connecting element may be embedded in a silicone elastomer layer or layers of the liner, or may be intimately bonded to the distal end of the liner. An example of such connecting element is discussed in U.S. Pat. No. 6,136,039.

The liners may be fabricated in a sufficient number of sizes to accommodate various sizes of residual limbs. In use, a liner of the type described herein is rolled up from the proximal to the distal end, placed over the distal end of the residual stump and rolled back up or "donned" over the stump like a stocking. This procedure and the benefits achieved thereby are described in detail in U.S. Pat. No. 4,923,474 granted May 8, 1990, incorporated herein by reference and owned by the assignee of the present application. In addition, any of the liners and sleeves mentioned herein may be constructed in the manner prescribed by U.S. Pat. No. 4,923,474.

The embodiments of the inventive liner of the present application may be constructed according to the molding methods described in U.S. Pat. No. 6,485,776, the entirety of which is incorporated herein by reference and owned by the assignee of the present application. In making the liners having peripheral profiles, such profiles may be imparted to the liner by appropriate molding techniques, such as female molds which have the impression of the desired peripheral profiles of the invention.

In FIGS. 25–28, embodiments of an orthotic or prosthetic sleeve are illustrated having peripheral profiles, as described above in connection with the embodiments of FIGS. 1–24. The orthotic or prosthetic sleeves shown in FIGS. 25–28 resemble the basic construction of any one of the aforementioned liners, or the orthotic or prosthetic sleeves described in U.S. Pat. No. 6,592,539 granted Jul. 15, 2003, the entirety of which is incorporated herein by reference and owned by the assignee of the present application.

As shown in FIGS. 25–27, an embodiment of a sleeve 118 defines an open-ended tubular sleeve, and has an axis I—I. The sleeve 118 includes a proximal portion 120, a distal portion 124 and a peripheral profile portion 122 axially extending between the proximal and distal portions 120 and 124.

The peripheral profiles 122 are defined as a plurality of projections 126 that extend annularly about the axis of the sleeve 118. The projections 126 have a generally uniform, rounded outline, and are each axially spaced from one another by a groove 128. As shown in FIGS. 26 and 27, the projections 126 and the grooves 128 generally distend radially beyond adjacent sections of the proximal and distal portions 120, 124, and an internal surface (not shown) of the sleeve 118 is substantially smooth. The proximal end of the sleeve 120 may include a sealed edge 130.

According to this embodiment of the sleeve, and as discussed in U.S. Pat. No. 6,592,539, the sleeve may include at least two elasticized fabric elements having different elastic stiffness in orthogonal directions connected together to form a tubular sleeve such that the direction of higher stiffness of one fabric element extends parallel with the sleeve axis and the direction of higher stiffness of the other element extends generally transversely of the sleeve axis. The entire internal surface of the sleeve may be coated with a discrete layer of silicone elastomer that is firmly bonded to the fabric material constituting the sleeve.

Figure 28:
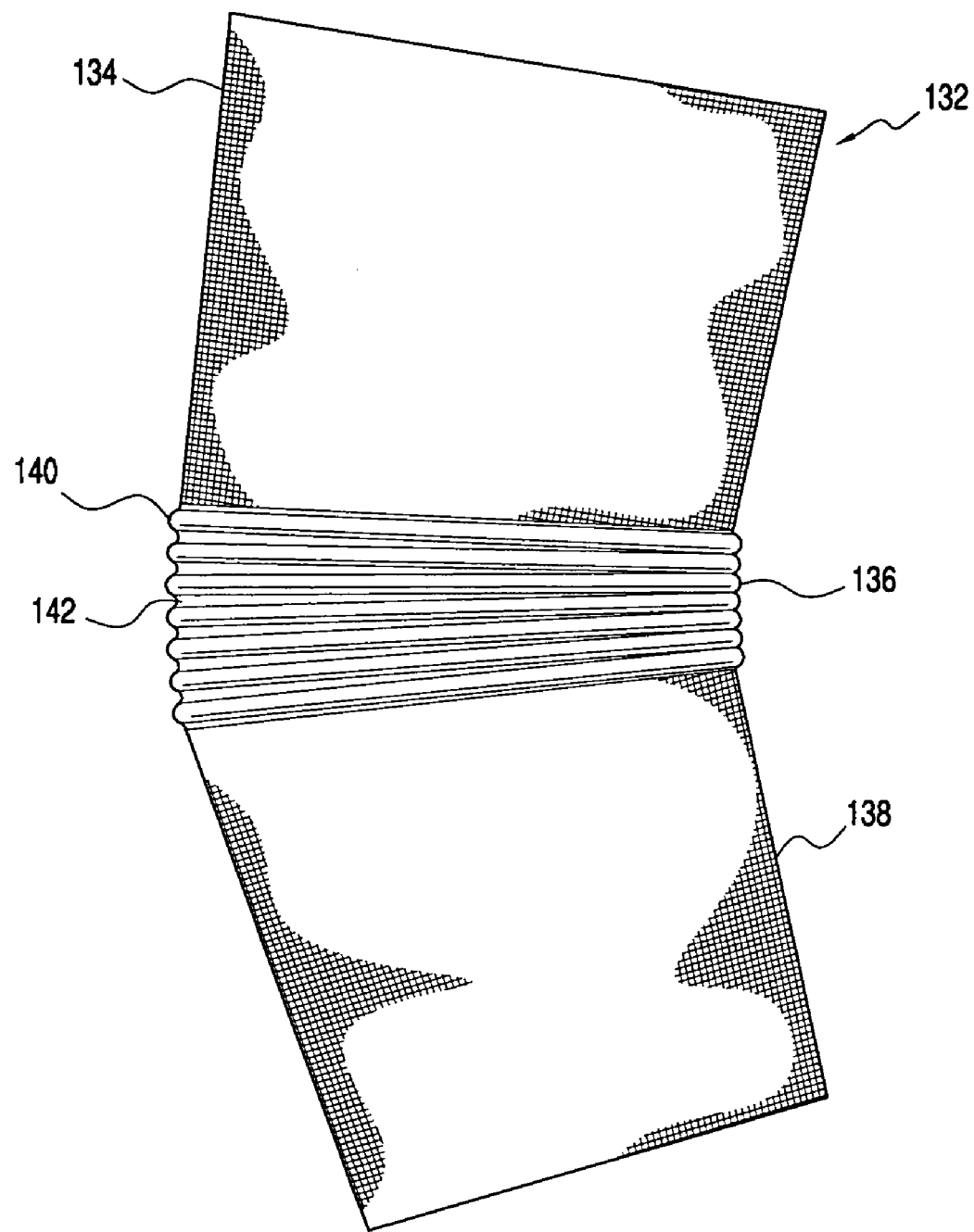
FIG. 28 is an elevational view of another version of a prosthetic or orthotic sleeve of the invention.

FIG. 28 illustrates another embodiment of a sleeve 132. This sleeve 132 includes at least three elasticized fabric elements, such that a proximal portion 134 and a distal portion 138 have higher elastic stiffness than a curved, middle peripheral profile portion 136 positioned between the proximal and distal portions 134, 138 and formed so that the direction of higher elastic stiffness of the fabric extends generally transversely of the sleeve axis.

The peripheral profile portion 136 includes a plurality of projections 140 and a plurality of grooves 142 interposed between each of the projections 140. The projections 140 and the grooves 142 may extend radially beyond the adjacent external surfaces of the proximal and distal portions 134, 138. The entire internal surface of the sleeve may be coated with a discrete layer of silicone elastomer that is firmly bonded to the fabric material constituting the sleeve.

Of note, this sleeve 132 is exemplary of a liner or sleeve according to this invention wherein the projections 140 are not uniformly spaced. Any of the liners or sleeves may be modified accordingly to provide localized regions having greater flexure.

In another variation of the embodiment of an open-ended tubular sleeve, FIGS. 29–32 show sleeve 200 having first and second peripheral profile portions 208, 214.

The first peripheral profile portion 208 is generally located within the center portion 204 of the sleeve 200 between the proximal and distal portions 202, 206. This peripheral profile portion 208 includes a plurality of undulating projections 210 extending radially outwardly about axis J—J, and corresponding grooves 212 interposed between the projections 210.

The second peripheral profile portion 214 is generally located within the proximal portion 202. The second peripheral profile portion 214 includes a plurality of undulating projections 216 that extend longitudinally generally along axis J—J, and circumferentially about axis J—J.

This sleeve 200 also includes a tapered portion 226 located along the distal portion 206. This tapered portion 226 has a generally uninterrupted surface such that it is smooth and without the undulating peripheral profile projections 208, 214 in the center and proximal portions 202, 204.

The proximal and center portions 202, 204 may have a slight taper such that the sleeve 200 gradually converges towards the axis J—J from the proximal end towards the distal end of the sleeve 200. The taper 226, however, is significantly more pronounced at the distal portion 206, as evidenced by the lines 228 showing the diameter of the sleeve at the boundary between the center and distal portions 204, 206 of the sleeve 200.

This tapered portion 226 is provided, at least in part, to more securely fit against prosthetic devices worn distally of a user of the sleeve. Moreover, since the proximal portion 202 may be worn over an upper leg portion, the tapered portion 226 provides a better fit to lower leg portions or prosthetic components since these tend to have a smaller diameter than an upper leg portion.

As shown in FIG. 32, the interior surface 220 of the sleeve 200 is shown. According to this embodiment, a plurality of proximal and distal sealing rings 222, 224 are formed by the thickness 218 of the sleeve 200. These sealing rings 222, 224 extend towards the axis J—J of the sleeve 200. The proximal and distal sealing rings 222, 224 are located in corresponding proximal and distal portions 202, 204 of the sleeve 200.

It will be noted that any of the suspension liner and sleeve embodiments discussed herein may be provided with the aforementioned sealing rings. These rings may be located within in any one of the proximal, distal and center portions of the suspension liners or sleeves described herein.

The sealing rings are advantageous in that they provide maximum sealing properties of the suspension liner or sleeve when worn against the skin. This is particularly beneficial when it is desired to provide an airtight seal between a residual limb of an amputee and a prosthesis socket worn by the amputee. Since these rings are preferably integrally formed by the silicone, they can conform to various shapes and sizes. In addition, the end sections of the proximal and distal portions of sleeve may be folded over to provide for a greater sealing effect by the sealing rings.

The embodiments of the sleeve may be provided with stiffening elements provided along the length of such sleeves with known principles to provide lateral rigidity to the sleeve, and in accordance with the principles taught in U.S. Pat. No. 6,592,539.

Variations of the embodiments of the liner and sleeve may have thicker wall thicknesses at areas such as at the proximal and distal ends of the proximal and distal portions. This is intended to strengthen these areas of the liner or sleeve. The variable wall thicknesses of these variations need not correspond to the peripheral profiled portions. Other areas of these variations may have thinner wall thicknesses relative to the proximal and distal ends at areas, and other areas of the liner or sleeve. The areas having thinner wall thicknesses are those that require less strength and are reduced in thickness in an effort to lessen the weight of the liner or sleeve.

When used with a distal locking device, this sleeve embodiment provides additional security to users. In some cases this embodiment can serve as a locking device in itself when used over a liner and definitive socket with a suction valve, ensuring that no air enters the definitive socket from above. As a result, this embodiment provides enhanced security and stability, added flexure at the knee, and strength and durability for high active users.

The embodiments of the liners and sleeves herein are not limited to use in a prosthesis system and may be applied in any suitable application requiring the features and advantages of the peripheral profiles and combinations thereof described above.

The invention is not considered to be limited to the peripheral profiles, protrusions and grooves described herein, but instead the configuration of the peripheral profiles, protrusions and grooves may be defined in a variety of configurations that may be considered to impart the aforementioned benefits of the present invention. The profiles may have any cross-sectional shape deemed to impart the benefits of the invention such as square, triangular, rectilinear, arcuate and combinations thereof. Also, the path of the profiles may not be generally linear as shown, but instead may not have a uniform size and instead may have varying cross-sectional sizes.

While the profiles are shown as extending about the entirety of the circumference of the liner and sleeve, these profiles may only extend about a portion of the circumference. For example, in the liner of FIG. 1, the projections only extend about an anterior portion corresponding to the anterior side of a residual limb. Alternatively, the sleeve of FIG. 28 may only have the projections on the anterior of the sleeve corresponding to the anterior side or a knee or prosthetic component.

It will be understood that, unless a term is expressly defined in this patent to possess a described meaning, there is no intent to limit the meaning of such term, either expressly or indirectly, beyond its plain or ordinary meaning.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, and equivalents falling within the spirit and scope of the disclosure as defined by the appended claims.

Any element in a claim that does not explicitly state "means for" performing a specified function, or "step for" performing a specific function, is not to be interpreted as a "means" or "step" clause as specified in 35 U.S.C. § 112, paragraph 6.

It will be understood that the above described embodiments of the invention are illustrative in nature, and that modifications thereof may occur to those skilled in the art. Accordingly, this invention is not to be regarded as limited to the embodiments disclosed herein, but is to be limited only as defined in the appended claims.

I claim:

1. A residual limb suspension liner for a prosthesis, comprising:
    a closed-ended, tubular sleeve having an axis, and defining along the axis a distal portion, a proximal portion, and a center portion extending between the distal and proximal portions;
    wherein an internal surface of the sleeve is defined by a continuously cured elastomeric material layer;
    wherein an external surface of the sleeve forms a non-peripheral profile portion having a uniform wall thickness and the external surface further forms at least one peripheral profile portion integrally formed from the elastomeric layer and having an undulating wall thickness extending into the proximal and center portions of the sleeve;
    wherein the maximum thickness of the undulating wall thickness is substantially the same as the non-peripheral profile portion uniform wall thickness.

2. The suspension liner according to claim 1, wherein the at least one peripheral profile portion defines a plurality of annular projections extending radially outwardly from and about the sleeve axis.

3. The suspension liner according to claim 2, wherein the plurality of projections are generally uniformly spaced from one another.

4. The suspension liner according to claim 1, wherein the at least one peripheral profile portion defines a plurality of longitudinal projections extending longitudinally along the sleeve about the circumference thereof.

5. The suspension liner according to claim 4, wherein the plurality of projections are generally uniformly spaced from one another.

6. The suspension liner according to claim 1, wherein the at least one peripheral profile portion defines a plurality of annular projections extending obliquely relative to the sleeve axis.

7. The suspension liner according to claim 1, wherein the external surface of the sleeve is arranged for direct contact against a hardened prosthetic socket.

8. The suspension liner according to claim 1, wherein the peripheral profile portion only extends in the proximal and center portions of the sleeve.

9. A residual limb suspension liner for a prosthesis, comprising:
    a closed-ended, tubular sleeve having an axis, and defining along the axis a distal portion, a proximal portion, and a center portion extending between the distal and proximal portions;
    wherein the tubular sleeve comprises a tubular shaped elastomeric layer defining an internal surface of the liner, and an elasticized fabric secured to the elastomeric layer, the elasticized fabric defining an external surface of the liner;
    wherein the external surface of the liner forms a non-peritheral profile portion having a uniform wall thickness and the external surface further forms at least one peripheral profile portion formed from the elastomeric layer and having an undulating wall thickness extending into the proximal and center portions of the sleeve;
    wherein the maximum thickness of the undulating wall thickness is substantially the same as the non-peripheral profile portion uniform wall thickness.

10. The suspension liner according to claim 9, wherein the at least one peripheral profile portion defines a plurality of annular projections extending radially outwardly from and about the sleeve axis.

11. The suspension liner according to claim 10, wherein the plurality of projections are generally uniformly spaced from one another.

12. The suspension liner according to claim 9, wherein the at least one peripheral profile portion comprises a plurality of longitudinal projections extending longitudinally along the sleeve about the circumference thereof.

13. The suspension liner according to claim 9, wherein the plurality of projections are generally uniformly spaced from one another.

14. The suspension liner according to claim 9, wherein the at least one peripheral profile portion comprises a plurality of annular projections extending obliquely relative to the sleeve axis.

15. The suspension liner according to claim 9, wherein the elasticized fabric has a higher stiffness along a first direction than along a second direction that is orthogonal to the first direction.

16. The suspension liner according to claim 9, wherein the external surface of the sleeve is arranged for direct contact against a hardened prosthetic socket.

17. The suspension liner according to claim 9, wherein the peripheral profile portion only extends in the proximal and center portions of the sleeve.

18. A residual limb suspension liner for a prosthesis, comprising:
    a closed-ended, tubular sleeve having an axis, and defining along the axis a distal portion, a proximal portion, and a center portion extending between the distal and proximal end portions;
    wherein the external surface of the liner defines a non-peripheral profile portion having a uniform wall thickness and the external surface further defines at least one peripheral profile portion having an undulating wall thickness;

wherein the maximum thickness of the undulating wall thickness is substantially the same as the non-peripheral profile portion uniform wall thickness;

wherein the at least one peripheral profile portion includes a plurality of annular projections extending radially outwardly from and about the sleeve axis generally along the center portion of the sleeve;

wherein the at least one peripheral profile portion further comprises a plurality of longitudinal projections extending longitudinally along the sleeve about the circumference thereof and generally along the proximal portion of the sleeve.

19. The suspension liner according to claim 18, wherein the external surface of the sleeve is arranged for direct contact against a hardened prosthetic socket.

20. The suspension liner according to claim 18, wherein the peripheral profile portion only extends in the proximal and center portions of the sleeve.

* * * * *